US010258280B2

(12) United States Patent
Justice et al.

(10) Patent No.: US 10,258,280 B2
(45) Date of Patent: Apr. 16, 2019

(54) WEARABLE ELECTRONIC DEVICE

(71) Applicant: MICROSOFT TECHNOLOGY LICENSING, LLC, Redmond, WA (US)

(72) Inventors: Gregory Kim Justice, Redmond, WA (US); Vinod L. Hingorani, Redmond, WA (US); Farah Shariff, Kirkland, WA (US); Stephen John Minarsch, Seattle, WA (US); Thomas E. McCue, Jr., Vancouver, WA (US); Amish Patel, Seattle, WA (US); Mark Shintaro Ando, Seattle, WA (US); Scott F. Williams, Redmond, WA (US); Mohammad Shakeri, Kirkland, WA (US); Byung J. Cho, Bellevue, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 969 days.

(21) Appl. No.: 14/292,551

(22) Filed: May 30, 2014

(65) Prior Publication Data

US 2015/0342525 A1     Dec. 3, 2015

(51) Int. Cl.
*A61B 5/00* (2006.01)
*A61B 5/024* (2006.01)
(Continued)

(52) U.S. Cl.
CPC .......... *A61B 5/6831* (2013.01); *A61B 5/0022* (2013.01); *A61B 5/0024* (2013.01);
(Continued)

(58) Field of Classification Search
CPC ... A61B 5/6831; A61B 5/0022; A61B 5/0024; A61B 5/02427; A61B 5/0531
See application file for complete search history.

(56) References Cited

U.S. PATENT DOCUMENTS

| 7,733,224 B2 | 6/2010 | Tran |
| 7,843,325 B2 * | 11/2010 | Otto ..................... A61B 5/0002 340/506 |

(Continued)

FOREIGN PATENT DOCUMENTS

| WO | 2012061440 A2 | 5/2012 |
| WO | 2012125425 A2 | 9/2012 |

(Continued)

OTHER PUBLICATIONS

Coxworth, Ben., "UV-measuring wrist band lets you know when to reapply sunscreen", Published on: Mar. 7, 2013 Available at: http://www.gizmag.com/uveband-uv-measuring-wrist-band/26559/.

(Continued)

*Primary Examiner* — Joseph M Dietrich
(74) *Attorney, Agent, or Firm* — Alleman Hall Creasman & Tuttle LLP

(57) ABSTRACT

A wearable electronic device includes a composite band, a touch-sensor display, a skin sensor, and a course of electrical conductors. The composite band forms a loop having two or more rigid segments and a flexible segment coupled between the rigid segments. The touch-sensor display is arranged in a first of the rigid segments, and a skin sensor is arranged in a second of the rigid segments. The course of electrical conductors runs between the first and second rigid segments, inside the flexible segment.

17 Claims, 5 Drawing Sheets

(51) Int. Cl.
  *A61B 7/04* (2006.01)
  *A61B 5/11* (2006.01)
  *G04G 21/02* (2010.01)
  *A61B 5/053* (2006.01)
  *G04G 17/04* (2006.01)
  *A61B 5/01* (2006.01)
  *G04G 21/08* (2010.01)

(52) U.S. Cl.
  CPC ........ *A61B 5/02427* (2013.01); *A61B 5/0531* (2013.01); *A61B 5/1112* (2013.01); *A61B 5/681* (2013.01); *A61B 5/742* (2013.01); *A61B 5/7405* (2013.01); *A61B 5/7475* (2013.01); *A61B 7/04* (2013.01); *G04G 17/04* (2013.01); *G04G 21/025* (2013.01); *A61B 5/01* (2013.01); *A61B 5/02438* (2013.01); *A61B 5/0533* (2013.01); *A61B 2560/0214* (2013.01); *A61B 2560/0242* (2013.01); *A61B 2560/0252* (2013.01); *A61B 2562/0214* (2013.01); *A61B 2562/0238* (2013.01); *A61B 2562/164* (2013.01); *G04G 21/08* (2013.01)

(56) References Cited

U.S. PATENT DOCUMENTS

| | | | |
|---|---|---|---|
| 8,181,881 B2 | 5/2012 | Pedicano | |
| 8,275,327 B2 | 9/2012 | Yi et al. | |
| 2007/0279852 A1* | 12/2007 | Daniel | A44C 5/0007 361/679.03 |
| 2008/0164999 A1 | 7/2008 | Otto | |
| 2008/0167573 A1 | 7/2008 | Stivoric et al. | |
| 2011/0098583 A1 | 4/2011 | Pandia et al. | |
| 2014/0078694 A1 | 3/2014 | Wissmar | |
| 2014/0142403 A1 | 5/2014 | Brumback et al. | |

FOREIGN PATENT DOCUMENTS

| | | |
|---|---|---|
| WO | 2012170110 A1 | 12/2012 |
| WO | 2013045983 A1 | 4/2013 |

OTHER PUBLICATIONS

"Talk about Timing: Apple's iWatch Patent Arrives", Published on: Feb. 21, 2013 Avialable at: http://www.patentlyapple.com/patently-apple/2013/02/talk-about-timing-apples-wristwatch-patent-arrives.html.

Wu, et al., "Conformal bluetooth antenna for the watch-type wireless communication device application", In IEEE Antenna and Propagation Society International Symposium, Jun. 9, 2007, 4 pages.

Fingas, Jon, "TomTom's new GPS watches track your heart rate without a chest strap (update: US pricing)", http://www.engadget.com/2014/04/03/tomtom-cardio-gps-watches/, Apr. 3, 2014, 10 pages.

Goode, Lauren, "Samsung's New Gear Fit Needs to Work on the "Fit" Part", http://recode.net/2014/04/08/samsungs-new-gear-fit-needs-to-work-on-the-fit-part/, Apr. 8, 2014, 10 pages.

"Samsung Gear Fit, Gear 2 and Gear 2 Neo go on sale worldwide", NDTV Gadgets, http://gadgets.ndtv.com/others/news/samsung-gear-fit-gear-2-and-gear-2-neo-go-on-sale-worldwide-507220, Apr. 11, 2014, 3 pages.

Poeter, Damon, "Meet Simband, Samsung's Next-Gen Health Tracker", http://www.pcmag.com/article2/0,2817,2458663,00.asp, May 28, 2014, 5 pages.

ISA European Patent Office, International Search Report and Written Opinion issued in Application No. PCT/US2015/033080, dated Oct. 28, 2015, WIPO, 11 pages.

"First Office Action Issued in Chinese Patent Application No. 201580028908.6", dated Jan. 31, 2019, 12 Pages.

* cited by examiner

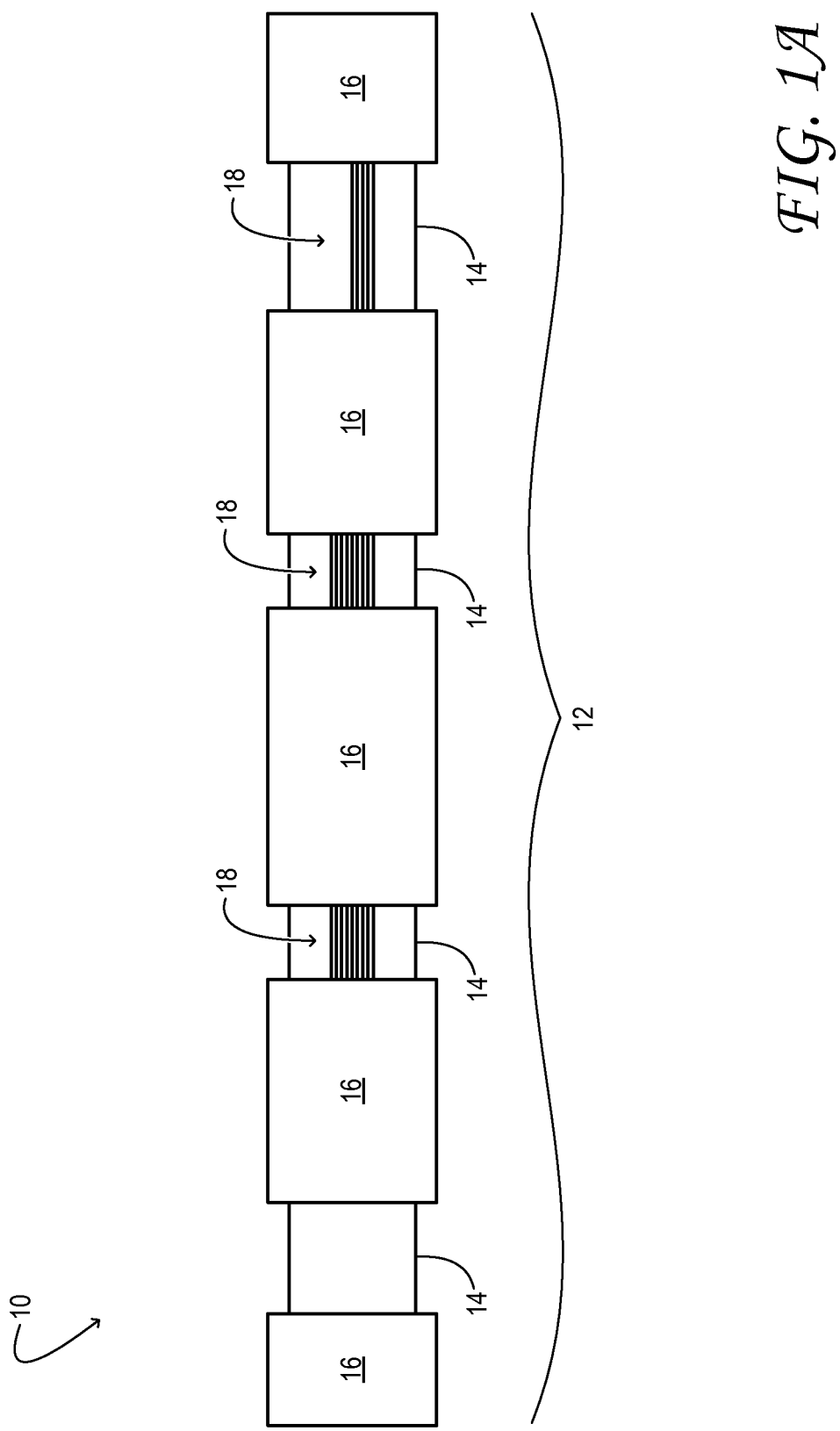

WEARABLE ELECTRONIC DEVICE

BACKGROUND

Numerous tradeoffs are considered in engineering an electronic device to be worn on the human body. Functionality, battery life, ergonomic comfort, and aesthetics, for example, all come into play. In some cases, the overall rigidity of traditionally engineered electronic structures is an obstacle to creating a functional, comfortable, and attractive device.

SUMMARY

One embodiment of this disclosure provides a wearable electronic device. The wearable electronic device includes a composite band, a touch-sensor display, a skin sensor, and a course of electrical conductors. The composite band forms a loop having two or more rigid segments and a flexible segment coupled between the rigid segments. The touch-sensor display is arranged in a first of the rigid segments, and a skin sensor is arranged in a second of the rigid segments. The course of electrical conductors runs between the first and second rigid segments, inside the flexible segment.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

FIG. 1A schematically shows aspects of an example wearable electronic device.

DETAILED DESCRIPTION

Figure 1B:
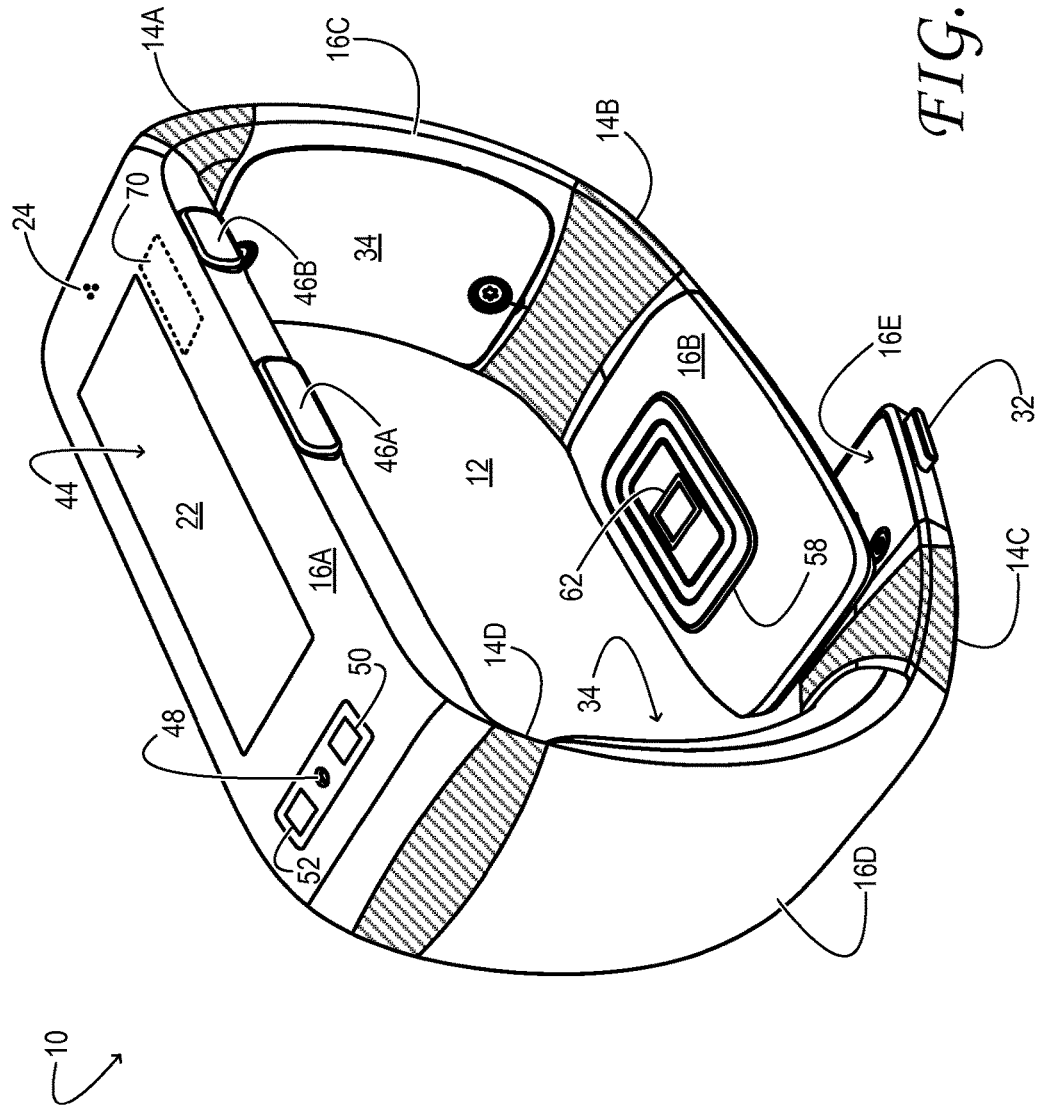
FIGS. 1B and 1C show additional aspects of an example wearable electronic device.

Aspects of this disclosure will now be described by example and with reference to the drawing figures listed above. Components and other elements that may be substantially the same in one or more figures are identified coordinately and described with minimal repetition. It will be noted, however, that elements identified coordinately may also differ to some degree.

Figure 1C:
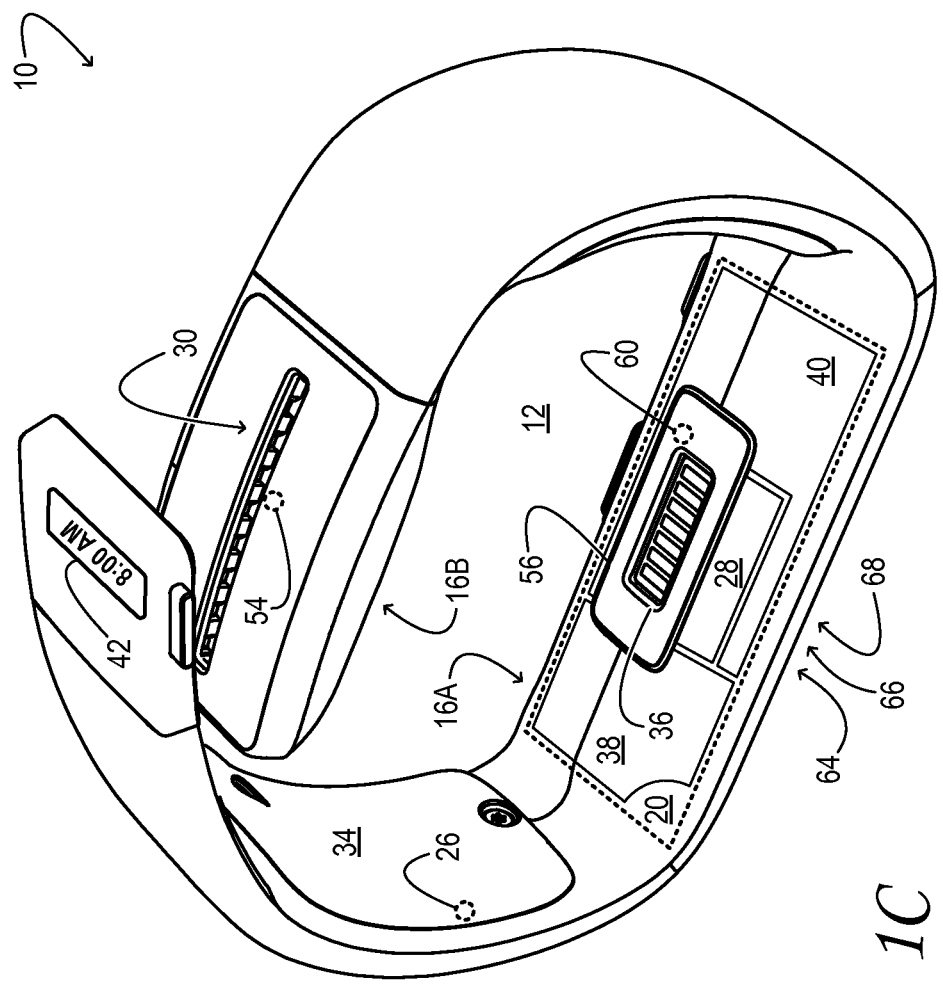

FIGS. 1A-C show aspects of a wearable electronic device 10 in one, non-limiting configuration. The illustrated device takes the form of a composite band 12, which may be worn around a wrist. Composite band 12 includes flexible segments 14 and rigid segments 16. The terms 'flexible' and 'rigid' are to be understood in relation to each other, not necessarily in an absolute sense. Moreover, a flexible segment may be relatively flexible with respect to one bending mode and/or stretching mode, while being relatively inflexible with respect to other bending modes, and to twisting modes. A flexible segment may be elastomeric in some examples. In these and other examples, a flexible segment may include a hinge and may rely on the hinge for flexibility, at least in part.

The illustrated configuration includes four flexible segments 14 linking five rigid segments 16. Other configurations may include more or fewer flexible segments, and more or fewer rigid segments. In some implementations, a flexible segment is coupled between pairs of adjacent rigid segments.

Various functional components, sensors, energy-storage cells, etc., of wearable electronic device 10 may be distributed among multiple rigid segments 16. Accordingly, as shown schematically in FIG. 1A, one or more of the intervening flexible segments 14 may include a course of electrical conductors 18 running between adjacent rigid segments, inside or through the intervening flexible segment. The course of electrical conductors may include conductors that distribute power, receive or transmit a communication signal, or carry a control or sensory signal from one functional component of the device to another. In some implementations, a course of electrical conductors may be provided in the form of a flexible printed-circuit assembly (FPCA, vide infra), which also may physically support various electronic and/or logic components.

In one implementation, a closure mechanism enables facile attachment and separation of the ends of composite band 12, so that the band can be closed into a loop and worn on the wrist. In other implementations, the device may be fabricated as a continuous loop resilient enough to be pulled over the hand and still conform to the wrist. Alternatively, the device may have an open bracelet form factor in which ends of the band are not fastened to one another. In still other implementations, wearable electronic devices of a more elongate band shape may be worn around the user's bicep, waist, chest, ankle, leg, head, or other body part. Accordingly, the wearable electronic devices here contemplated include eye glasses, a head band, an arm-band, an ankle band, a chest strap, or even an implantable device to be implanted in tissue.

As shown in FIGS. 1B and 1C, wearable electronic device 10 includes various functional components: a compute system 20, display 22, loudspeaker 24, haptic motor 26, communication suite 28, and various sensors. In the illustrated implementation, the functional components are integrated into rigid segments 16—viz., display-carrier module 16A, pillow 16B, battery compartments 16C and 16D, and buckle 16E. This tactic protects the functional components from physical stress, from excess heat and humidity, and from exposure to water and substances found on the skin, such as sweat, lotions, salves, and the like.

In the illustrated conformation of wearable electronic device 10, one end of composite band 12 overlaps the other end. A buckle 16E is arranged at the overlapping end of the composite band, and a receiving slot 30 is arranged at the overlapped end. As shown in greater detail herein, the receiving slot has a concealed rack feature, and the buckle includes a set of pawls to engage the rack feature. The buckle snaps into the receiving slot and slides forward or backward for proper adjustment. When the buckle is pushed into the slot at an appropriate angle, the pawls ratchet into tighter fitting set points. When release buttons 32 are squeezed simultaneously, the pawls release from the rack feature, allowing the composite band to be loosened or removed.

The functional components of wearable electronic device 10 draw power from one or more energy-storage cells 34. A battery—e.g., a lithium ion battery—is one type of energy-storage cell suitable for this purpose. Examples of alternative energy-storage cells include super- and ultra-capacitors. A typical energy storage cell is a rigid structure of a size that scales with storage capacity. To provide adequate storage capacity with minimal rigid bulk, a plurality of discrete separated energy storage cells may be used. These may be arranged in battery compartments 16C and 16D, or in any of the rigid segments 16 of composite band 12. Electrical connections between the energy storage cells and the functional components are routed through flexible segments 14. In some implementations, the energy storage cells have a curved shape to fit comfortably around the wearer's wrist, or other body part.

In general, energy-storage cells 34 may be replaceable and/or rechargeable. In some examples, recharge power may be provided through a universal serial bus (USB) port 36, which includes a magnetic latch to releasably secure a complementary USB connector. In other examples, the energy storage cells may be recharged by wireless inductive or ambient-light charging. In still other examples, the wearable electronic device may include electro-mechanical componentry to recharge the energy storage cells from the user's adventitious or purposeful body motion. More specifically, the energy-storage cells may be charged by an electromechanical generator integrated into wearable electronic device 10. The generator may be actuated by a mechanical armature that moves when the user is moving.

In wearable electronic device 10, compute system 20 is housed in display-carrier module 16A and situated below display 22. The compute system is operatively coupled to display 22, loudspeaker 24, communication suite 28, and to the various sensors. The compute system includes a data-storage machine 38 to hold data and instructions, and a logic machine 40 to execute the instructions.

Display 22 may be any suitable type of display, such as a thin, low-power light emitting diode (LED) array or a liquid-crystal display (LCD) array. Quantum-dot display technology may also be used. Suitable LED arrays include organic LED (OLED) or active matrix OLED arrays, among others. An LCD array may be actively backlit. However, some types of LCD arrays—e.g., a liquid crystal on silicon, LCOS array—may be front-lit via ambient light. Although the drawings show a substantially flat display surface, this aspect is by no means necessary, for curved display surfaces may also be used. In some use scenarios, wearable electronic device 10 may be worn with display 22 on the front of the wearer's wrist, like a conventional wristwatch. However, positioning the display on the back of the wrist may provide greater privacy and ease of touch input. To accommodate use scenarios in which the device is worn with the display on the back of the wrist, an auxiliary display module 42 may be included on the rigid segment opposite display-carrier module 16A. The auxiliary display module may show the time of day, for example.

Communication suite 28 may include any appropriate wired or wireless communications componentry. In FIGS. 1B and 1C, the communications suite includes USB port 36, which may be used for exchanging data between wearable electronic device 10 and other computer systems, as well as providing recharge power. The communication suite may further include two-way Bluetooth, Wi-Fi, cellular, near-field communication, and/or other radios. In some implementations, the communication suite may include an additional transceiver for optical, line-of-sight (e.g., infrared) communication.

In wearable electronic device 10, touch-screen sensor 44 is coupled to display 22 and configured to receive touch input from the user. Accordingly, the display may be a touch-sensor display in some implementations. In general, the touch sensor may be resistive, capacitive, or optically based. Push-button sensors (e.g., microswitches) may be used to detect the state of push buttons 46A and 46B, which may include rockers. Input from the push-button sensors may be used to enact a home-key or on-off feature, control audio volume, microphone, etc.

FIGS. 1B and 1C show various other sensors of wearable electronic device 10. Such sensors include microphone 48, visible-light sensor 50, ultraviolet sensor 52, and ambient-temperature sensor 54. The microphone provides input to compute system 20 that may be used to measure the ambient sound level or receive voice commands from the user. Input from the visible-light sensor, ultraviolet sensor, and ambient-temperature sensor may be used to assess aspects of the user's environment. In particular, the visible-light sensor can be used to sense the overall lighting level, while the ultraviolet sensor senses whether the device is situated indoors or outdoors. In some scenarios, output from the visible light sensor may be used to automatically adjust the brightness level of display 22, or to improve the accuracy of the ultraviolet sensor. In the illustrated configuration, the ambient-temperature sensor takes the form a thermistor, which is arranged behind a metallic enclosure of pillow 16B, next to receiving slot 30. This location provides a direct conductive path to the ambient air, while protecting the sensor from moisture and other environmental effects.

FIGS. 1B and 1C show a pair of contact sensors—charging contact sensor 56 arranged on display-carrier module 16A, and pillow contact sensor 58 arranged on pillow 16B. Each contact sensor contacts the wearer's skin when wearable electronic device 10 is worn. The contact sensors may include independent or cooperating sensor elements, to provide a plurality of sensory functions. For example, the contact sensors may provide an electrical resistance and/or capacitance sensory function responsive to the electrical resistance and/or capacitance of the wearer's skin. To this end, the two contact sensors may be configured as a galvanic skin-response sensor, for example. Compute system 20 may use the sensory input from the contact sensors to assess whether, or how tightly, the device is being worn, for example. In the illustrated configuration, the separation between the two contact sensors provides a relatively long electrical path length, for more accurate measurement of skin resistance. In some examples, a contact sensor may also provide measurement of the wearer's skin temperature. In the illustrated configuration, a skin temperature sensor 60 in the form a thermistor is integrated into charging contact sensor 56, which provides direct thermal conductive path to the skin. Output from ambient-temperature sensor 54 and skin temperature sensor 60 may be applied differentially to estimate of the heat flux from the wearer's body. This metric can be used to improve the accuracy of pedometer-based calorie counting, for example. In addition to the contact-based skin sensors described above, various types of non-contact skin sensors may also be included.

Arranged inside pillow contact sensor 58 in the illustrated configuration is an optical pulse-rate sensor 62. The optical pulse-rate sensor may include a narrow-band (e.g., green) LED emitter and matched photodiode to detect pulsating blood flow through the capillaries of the skin, and thereby provide a measurement of the wearer's pulse rate. In some implementations, the optical pulse-rate sensor may also be configured to sense the wearer's blood pressure. In the illustrated configuration, optical pulse-rate sensor 62 and display 22 are arranged on opposite sides of the device as worn. The pulse-rate sensor alternatively could be positioned directly behind the display for ease of engineering. In some implementations, however, a better reading is obtained when the sensor is separated from the display.

Wearable electronic device 10 may also include motion sensing componentry, such as an accelerometer 64, gyroscope 66, and magnetometer 68. The accelerometer and gyroscope may furnish inertial data along three orthogonal axes as well as rotational data about the three axes, for a combined six degrees of freedom. This sensory data can be used to provide a pedometer/calorie-counting function, for example. Data from the accelerometer and gyroscope may be combined with geomagnetic data from the magnetometer to further define the inertial and rotational data in terms of geographic orientation.

Wearable electronic device 10 may also include a global positioning system (GPS) receiver 70 for determining the wearer's geographic location and/or velocity. In some configurations, the antenna of the GPS receiver may be relatively flexible and extend into flexible segment 14A. In the configuration of FIGS. 1B and 1C, the GPS receiver is far removed from optical pulse-rate sensor 62 to reduce interference from the optical pulse-rate sensor. More generally, various functional components of the wearable electronic device—display 22, compute system 20, GPS receiver 70, USB port 36, microphone 48, visible-light sensor 50, ultraviolet sensor 52, and skin temperature sensor 60—may be located in the same rigid segment for ease of engineering, but the optical pulse-rate sensor may be located elsewhere to reduce interference on the other functional components.

Figure 2B:
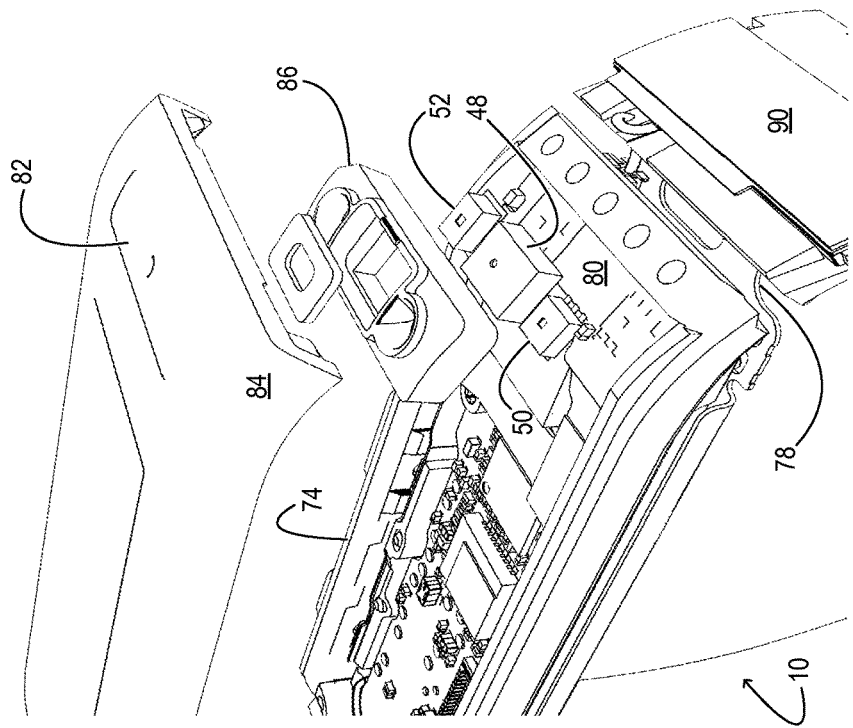
FIGS. 2A and 2B are exploded views of an example wearable electronic device.
Figure 2A:
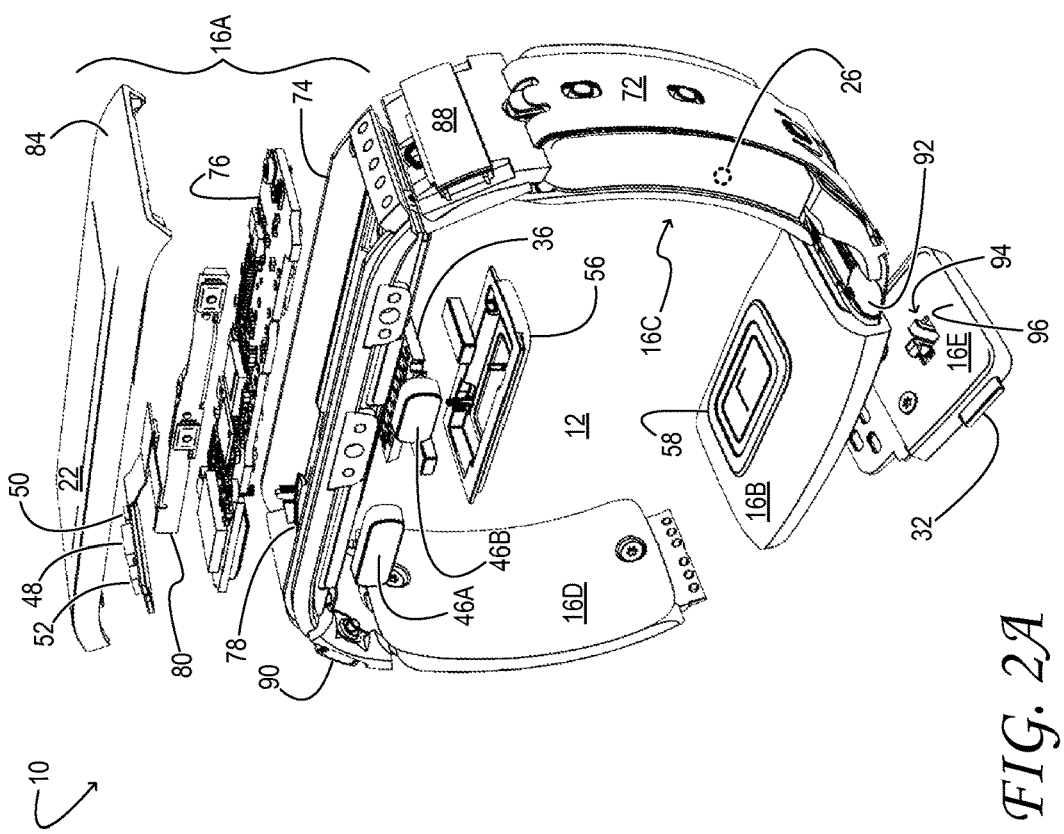

FIGS. 2A and 2B show aspects of the internal structure of wearable electronic device 10 in one, non-limiting configuration. In particular, FIG. 2A shows semi-flexible armature 72 and display carrier 74. The semi-flexible armature is the backbone of composite band 12, which supports display-carrier module 16A, pillow 16B, and battery compartments 16B and 16C. The semi-flexible armature may be a very thin band of steel, in one implementation. The display carrier may be a metal frame overmolded with plastic. It may be attached to the semi-flexible armature with mechanical fasteners. In one implementation, these fasteners are molded-in rivet features, but screws or other fasteners may be used instead. The display carrier provides suitable stiffness in display-carrier module 16A to protect display 22 from bending or twisting moments that could dislodge or break it. In the illustrated configuration, the display carrier also surrounds the main printed circuit assembly (PCA) 76, where compute system 20 is located, and provides mounting features for the main PCA.

In some implementations, wearable electronic device 10 includes a main flexible FPCA 78, which runs from pillow 16B all the way to battery compartment 16D. In the illustrated configuration, the main FPCA is located beneath semi-flexible armature 72 and assembled onto integral features of the display carrier. In the configuration of FIG. 2A, push buttons 46A and 46B penetrate one side of display carrier 74. These push buttons are assembled directly into the display carrier and are sealed by o-rings. The push buttons act against microswitches mounted to sensor FPCA 80.

Display-carrier module 16A also encloses sensor FPCA 80. At one end of rigid segment 16A, and located on the sensor FPCA, are visible-light sensor 50, ultraviolet sensor 52, and microphone 48. A polymethylmethacrylate window 82 is insert molded into a glass insert-molded (GIM) bezel 84 of display-carrier module 16A, over these three sensors. The window has a hole for the microphone and is printed with IR transparent ink on the inside covering except over the ultraviolet sensor. A water repellent gasket 86 is positioned over the microphone, and a thermoplastic elastomer (TPE) boot surrounds all three components. The purpose of the boot is to acoustically seal the microphone and make the area more cosmetically appealing when viewed from the outside.

As noted above, display carrier 74 may be overmolded with plastic. This overmolding does several things. First, the overmolding provides a surface that the device TPE overmolding will bond to chemically. Second, it creates a shut-off surface, so that when the device is overmolded with TPE, the TPE will not ingress into the display carrier compartment. Finally, the PC overmolding creates a glue land for attaching the upper portion of display-carrier module 16A.

The charging contacts of USB port 36 are overmolded into a plastic substrate and reflow soldered to main FPCA 78. The main FPCA may be attached to the inside surface of semi-flexible armature 72. In the illustrated configuration, charging contact sensor 56 is frame-shaped and surrounds the charging contacts. It is attached to the semi-flexible armature directly under display carrier 74—e.g., with rivet features. Skin temperature sensor 60 (not shown in FIG. 2A or 2B) is attached to the main FPCA under the charging contact-sensor frame, and thermal conduction is maintained from the frame to the sensor with thermally conductive putty.

FIGS. 2A and 2B also show a Bluetooth antenna 88 and a GPS antenna 90, which are coupled to their respective radios via shielded connections. Each antenna is attached to semi-flexible armature 72 on either side of display carrier 74. The semi-flexible armature may serve as a ground plane for the antennas, in some implementations. Formed as FPCAs and attached to plastic antenna substrates with adhesive, the Bluetooth and GPS antennas extend into flexible segments 14A and 14D, respectively. The plastic antenna substrates maintain about a 2-millimeter spacing between the semi-flexible armature and the antennae, in some examples. The antenna substrates may be attached to semi-flexible armature 72 with heat staked posts. TPE filler parts are attached around the antenna substrates. These TPE filler parts may prevent TPE defects like 'sink' when the device is overmolded with TPE.

Shown also in FIG. 2A are a metallic battery compartments 16C and 16D, attached to the inside surface of semi-flexible armature 72, such that main FPCA 78 is sandwiched between the battery compartments and the semi-flexible armature. The battery compartments have an overmolded rim that serves the same functions as the plastic overmolding previously described for display carrier 74. The battery compartments may be attached with integral rivet features molded-in. In the illustrated configuration, battery compartment 16C also encloses haptic motor 26.

Shown also in FIG. 2A, a bulkhead 92 is arranged at and welded to one end of semi-flexible armature 72. This feature is shown in greater detail in the exploded view of FIG. 3. The bulkhead provides an attachment point for pillow contact sensor 58. The other end of the semi-flexible armature extends through battery compartment 16D, where flexible strap 14C is attached. The strap is omitted from FIG. 2 for clarity, but is shown in FIGS. 1B and 1C. In one example, the strap is attached with rivets formed integrally in the battery compartment. In another embodiment, a plastic end part of the strap is molded-in as part of the battery compartment overmolding process.

In the configuration of FIG. 2A, buckle 16E is attached to the other end of strap 14C. The buckle includes two opposing, spring-loaded pawls 94 constrained to move laterally in a sheet-metal spring box 96. The pawls and spring box are concealed by the buckle housing and cover, which also have attachment features for the strap. The two release buttons 32 protrude from opposite sides of the buckle housing. When these buttons are depressed simultaneously, they release the pawls from the track of receiving slot 30 (as shown in FIG. 1C).

Figure 3:
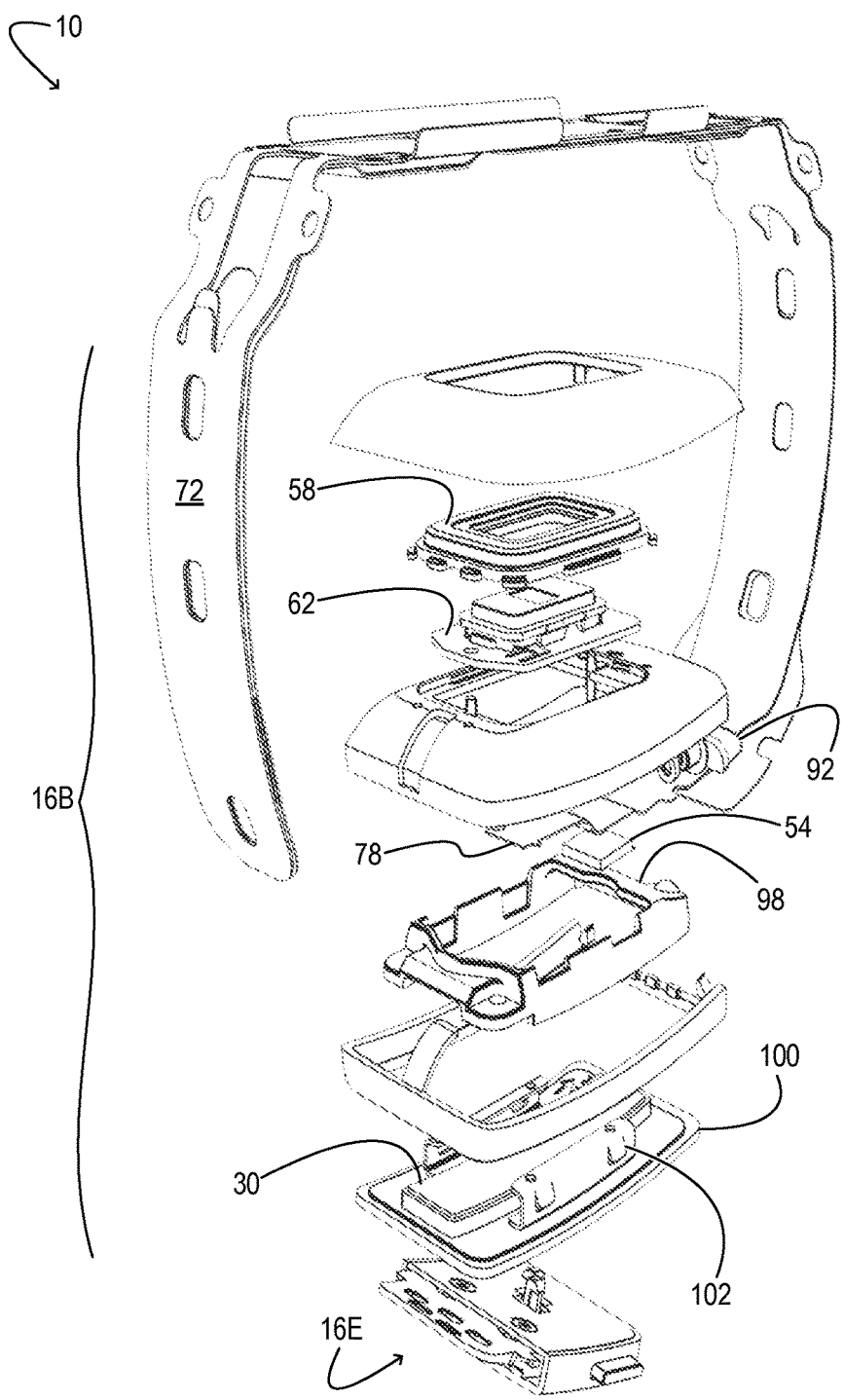
FIG. 3 is an exploded view of a portion of an example wearable electronic device.

Turning now to FIG. 3, pillow 16B includes pillow contact sensor 58, which surrounds optical pulse-rate sensor 62. The pillow also includes TPE and plastic overmoldings, an internal structural pillow case 98, and a sheet-metal or MIMS inner band 100. The pillow assembly is attached to bulkhead 92 with adhesives for sealing out water and by two screws that clamp the pillow case and the plastic overmolding securely to the bulkhead. The inner band includes receiving slot 30 and its concealed rack feature. In the illustrated configuration, the inner band is attached to the pillow via adhesives for water sealing and spring steel snaps 102, which are welded to the inside of the inner band on either side of the concealed rack. Main FPCA 78 extends through the bulkhead and into the pillow assembly, to pillow contact sensor 58. Ambient-temperature sensor 54 is attached to this FPCA and surrounded by a small plastic frame. The frame contains thermal putty to help maintain a conduction path through the inner band to the sensor. On the opposite side of the FPCA from the sensor a foam spring may be used to push the sensor, its frame, and thermal putty against the inside surface of the inner band.

Compute system 20, via the sensory functions described herein, may be configured to acquire various forms of information about the wearer of wearable electronic device 10. Such information must be acquired and used with utmost respect for the wearer's privacy. Accordingly, the sensory functions may be enacted subject to opt-in participation of the wearer. In implementations where personal data is collected on the device and transmitted to a remote system for processing, that data may be anonymized. In other examples, personal data may be confined to the wearable electronic device, and only non-personal, summary data transmitted to the remote system.

It will be understood that the configurations and approaches described herein are exemplary in nature, and that these specific implementations or examples are not to be taken in a limiting sense, because numerous variations are feasible. The specific routines or methods described herein may represent one or more processing strategies. As such, various acts shown or described may be performed in the sequence shown or described, in other sequences, in parallel, or omitted.

The subject matter of this disclosure includes all novel and non-obvious combinations and sub-combinations of the various processes, systems and configurations, and other features, functions, acts, and/or properties disclosed herein, as well as any and all equivalents thereof.

The invention claimed is:

1. A wearable electronic device comprising:
   a band including one or more flexible segments;
   a rigid display-carrier segment attached to at least one of the one or more flexible segments of the band;
   a rigid pillow segment attached at one end of the band to at least one of the one or more flexible segments of the band, the rigid pillow segment being configured to reversibly engage an opposite end of the band to form a loop;
   a computer, a touch-sensor display, and a first portion of a galvanic skin-response sensor arranged in the display-carrier segment;
   a second portion of the galvanic skin-response sensor arranged in the pillow segment, wherein the galvanic skin-response sensor is configured to assess tightness of the band on a wearer by measuring resistance between the first and second portions of the galvanic skin-response sensor; and
   a course of electrical conductors running between the display-carrier and pillow segments, through the one or more flexible segments.

2. The wearable electronic device of claim 1 further comprising an energy-storage cell arranged outside of the display-carrier and pillow segments.

3. The wearable electronic device of claim 2 wherein the band includes a third rigid segment in which the energy-storage cell is arranged and a fourth rigid segment in which another energy-storage cell is arranged.

4. The wearable electronic device of claim 1 wherein the galvanic skin-response sensor releases an output responsive to a resistance and/or capacitance of skin on which the wearable electronic device is worn.

5. The wearable electronic device of claim 1 wherein the computer is operatively coupled to the touch-sensor display and to the galvanic skin-response sensor.

6. The wearable electronic device of claim 1 further comprising one or more of an ambient-temperature sensor and a skin-temperature sensor arranged in a rigid segment and operatively coupled to the computer.

7. The wearable electronic device of claim 1 further comprising one or more of a visible light sensor and an ultraviolet sensor arranged in a rigid segment and operatively coupled to the computer.

8. The wearable electronic device of claim 1 further comprising one or more of a microphone and loudspeaker arranged in a rigid segment and operatively coupled to the computer.

9. The wearable electronic device of claim 1 further comprising a buckle receiver arranged on the pillow segment and a buckle arranged at the opposite end of the band relative to the pillow segment, wherein the loop is closed by receipt of the buckle into the buckle receiver.

10. A wearable electronic device comprising:
    a band including one or more flexible segments;
    a rigid display-carrier segment attached to at least one of the one or more flexible segments of the band;
    a rigid pillow segment attached at one end of the band to at least one of the one or more flexible segments of the band, the rigid pillow segment being configured to reversibly engage an opposite end of the band to form a loop;
    a computer, a touch-sensor display, and a contact sensor arranged in the display-carrier segment;
    an optical pulse rate sensor arranged in the pillow segment, wherein the contact sensor is configured to assess tightness of the optical pulse rate sensor against a wearer's skin; and
    a course of electrical conductors running between the display-carrier and pillow segments, through the one or more flexible segments.

11. The wearable electronic device of claim 10 further comprising a set of buttons arranged in the pillow segment and configured to release a set of spring-loaded pawls from a concealed rack feature.

12. A wearable electronic device comprising:
a band including one or more flexible segments;
a rigid display-carrier segment attached to at least one of the one or more flexible segments of the band;
a rigid pillow segment attached at one end of the band to at least one of the one or more flexible segments of the band, the rigid pillow segment being configured to reversibly engage an opposite end of the band to form a loop;
a computer, a touch-sensor display, a radio, and a first portion of a galvanic skin-response sensor arranged in the display-carrier segment;
an antenna coupled to the radio and extending from the display-carrier segment into a flexible segment of the one or more flexible segments;
a semi-flexible, metallic armature supporting the display-carrier segment and passing through the flexible segment, the semi-flexible armature being a ground plane for the radio antenna;
a second portion of the galvanic skin-response sensor arranged in the pillow segment, wherein the galvanic skin-response sensor is configured to assess tightness of the band on a wearer by measuring resistance between the first and second portions of the galvanic skin-response sensor; and
a course of electrical conductors running between the display-carrier and pillow segments, through the one or more flexible segments.

13. The wearable electronic device of claim 12 wherein the semi-flexible, metallic armature is a thin steel band.

14. The wearable electronic device of claim 12 wherein the radio is a global positioning system (GPS) receiver.

15. The wearable electronic device of claim 12 wherein the radio is a Bluetooth radio.

16. The wearable electronic device of claim 12 wherein the radio is one of a plurality of radios coupled to a corresponding plurality of antennae that extend into one or more flexible segments of the band.

17. The wearable electronic device of claim 12 wherein the antenna is maintained at least two millimeters from the semi-flexible, metallic armature.

* * * * *